US010478518B2

(12) United States Patent
Winterton (10) Patent No.: US 10,478,518 B2
(45) Date of Patent: Nov. 19, 2019

(54) METHOD FOR DISINFECTING CONTACT LENSES

(71) Applicant: Better Vision Solutions LLC, Keller, TX (US)

(72) Inventor: Lynn Winterton, Keller, TX (US)

(73) Assignee: Better Vision Solutions LLC, Keller, TX (US)

( * ) Notice: Subject to any disclaimer, the term of this patent is extended or adjusted under 35 U.S.C. 154(b) by 137 days.

(21) Appl. No.: 15/058,241

(22) Filed: Mar. 2, 2016

(65) Prior Publication Data

US 2017/0252478 A1   Sep. 7, 2017

(51) Int. Cl.
| *A61L 12/12* | (2006.01) |
| *A01N 59/00* | (2006.01) |
| *A61L 12/08* | (2006.01) |
| *C11D 3/00* | (2006.01) |

(52) U.S. Cl.
CPC ............ *A61L 12/124* (2013.01); *A01N 59/00* (2013.01); *A61L 12/086* (2013.01); *A61L 12/088* (2013.01); *A61L 12/126* (2013.01); *A61L 12/128* (2013.01); *C11D 3/0078* (2013.01)

(58) Field of Classification Search
CPC .............................. A61L 12/126; A61L 12/124
See application file for complete search history.

(56) References Cited

U.S. PATENT DOCUMENTS

| 3,912,451 | A | * | 10/1975 | Gaglia, Jr. ............ A61L 12/128 134/42 |
| 4,757,014 | A | | 7/1988 | Hendrickson et al. |
| 4,812,173 | A | | 3/1989 | Tsao et al. |
| 5,306,352 | A | * | 4/1994 | Nicolson ................ A01N 59/00 134/42 |
| 5,362,647 | A | * | 11/1994 | Cook ..................... A61L 12/126 422/30 |
| 6,945,389 | B2 | | 9/2005 | Scherer et al. |
| 8,410,011 | B2 | | 4/2013 | Huddersman et al. |
| 8,513,303 | B2 | | 8/2013 | Huddersman et al. |
| 8,767,367 | B2 | | 7/2014 | Higuchi et al. |
| 2002/0127281 | A1 | | 9/2002 | Tsao |
| 2011/0098174 | A1 | | 4/2011 | Huddersman |
| 2011/0114517 | A1 | | 5/2011 | Minick et al. |
| 2014/0366917 | A1 | * | 12/2014 | Yaacobi ................. A61L 12/128 134/18 |

FOREIGN PATENT DOCUMENTS

| WO | 90/14848 A1 | 12/1990 |
| WO | 2014012949 A1 | 1/2014 |

OTHER PUBLICATIONS

International Search Report & Written Opinion, dated May 15, 2017 cited in PCT/US2017/019933, 13 pages.
Kilvington, Simon and Winterton, Lynn: Fibrous Catalyst-Enhanced Acanthamoeba Disinfection by Hydrogen Peroxide, Optom Vis Sci 2017; 94(11):022-1028.

* cited by examiner

*Primary Examiner* — Donald R Spamer
(74) *Attorney, Agent, or Firm* — Merchant & Gould P.C.

(57) ABSTRACT

A method for disinfecting contact lenses, including immersing the contact lenses in a volume of cleaning agent with about 3% hydrogen peroxide for up to 4 hrs, and immersing up to 0.7 g of a fibrous catalyst enhancer material in the volume of cleaning agent for up to 4 hrs. The fibrous catalyst enhancer material is immersed simultaneously with the contact lenses.

27 Claims, 8 Drawing Sheets

METHOD FOR DISINFECTING CONTACT LENSES

TECHNICAL FIELD

The present disclosure generally relates to disinfecting contact lenses. More specifically, the present disclosure relates to disinfecting contact lenses with hydrogen peroxide.

BACKGROUND

*Acanthamoeba* species were first found in an ocular infection in 1973. Since that initial non-contact lens associated case of infection (*Acanthamoeba Keratitis* or AK), most cases have been associated with contact lens wear. The first documented series of cases were associated with the use of water with salt tablets, with enzyme tablets or wearing lenses while swimming or in a hot tub. Following those incidents, the annual rate of infection in the United States was reported by Schaumberg and co-workers in 1988 as approximately 2 cases per million. In the UK, Seal reported in 2003 levels at one per thirty thousand (approximately 33/million) as the base line value. The incidence rate most often quoted for the UK incidence is 20 per million.

During 2005-2007, workers at the University of Illinois Chicago (UIC) reported an outbreak that was referred to the Centers for Disease Control (CDC). CDC initiated a multistate investigation. An expanded investigation by CDC indicated that the risk of *Acanthamoeba keratitis* (AK) was increased in the use of a single product, Abbott Medical Optic's (AMO) Complete Multi-Plus. The reported correlation with this specific product was attributed to components of the formulation causing the organism to go from the trophozoite form to the cyst. The cyst is more resistant to most disinfection options.

Since the withdrawal of the AMO product, the incidence in the US has not returned to the levels reported in a 1998 study by D. Schaumberg based on the results of a review of the incidence from key ophthalmology centers. The current rate is estimated to be in the order of 12-20 cases per million in the US. CDC has continued to follow up on the incidence of AK.

It has been hypothesized that this is a result of changes in the treatment of potable water. The levels of chlorine used for disinfection were decreased to reduce the incidence of chlorinated by-products.

Understanding the exposure rates for contact lens wearers from the environment is important in developing approaches to testing products for disinfection efficacy. Researchers especially in the UK have regularly reported significant evidence of contamination of the water supplies in homes usually using techniques which swab the inside of the pipes and faucets in homes especially in "stored" water. However, environmental studies in the US have showed low levels of organisms in the water column in lakes and rivers, often measured in organisms per 100-200 ml. Levels were often below ten. A study carried out in the water supplies in Fort Worth, Tex. and presented at the University of Houston showed no organisms in "grab" samples during storm-free periods from lakes used as public water supply. Low levels of *Acanthamoeba* were detected after rain periods with significant run off, and in small ponds without significant water flow. In the same study, no *Acanthamoeba* were recovered from flowing water from homes.

The primary standard to test microbiocidal disinfection efficacy of contact lens care products is ISO 14729.13 This standard calls out the testing against 5 organisms, two gram negative bacteria, *Pseudomonas aeruginosa*, and *Serratia marcescens*, a gram positive bacteria, *Staph. aureus*, a yeast, *Candida albicans*, and a mold *Fusarium solani*. During the development of this standard in the 1990's (developed after the outbreak of the 1980's), a discussion was included for the reason the *Acanthamoeba* was not included as a part of this test protocol. In 2014 a second standard ISO 18259: 2014 has been put in place under ISO testing care products in the presence of lenses and cases. This new standard includes the same five organisms as ISO 14729. *Acanthamoeba* is not included as a test organism in the new standard.

The ISO disinfection standard 14729 has been the primary standard accepted by most jurisdictions around the world. The United States under FDA has currently no separate standard, and this standard is included in the ANSI Z-80-18 standard on contact lens care product.

After the 2007 incident first observed at UIC, there have been a number of approaches to evaluate efficacy against various species of this genus. During discussions carried out at a Workshop sponsored by the FDA in January 2009, a single item received a consensus recommendation to be included into a testing standard. This was a measure of conversion of trophozoites to cysts (or encystment). This has been included in an ISO standard (ISO19045) which published in 2015. This new standard does not include any acceptance criteria although the difference between the positive control (greater than 30% encystment) and negative controls (less than 5% controls) were observed in the inter-laboratory of this standard.

The development of measurements of disinfection efficacy has had much more difficulty. A number of *Acanthamoeba* species have been examined using a variety of organism growth conditions, test conditions and recovery techniques. These difference have led a variety of results for individual care products. Only recently has a single approach to determination of trophozoites has been selected by experts on ISO TC172/SC7/WG9 for validation using 2 species. The experts were in the process of developing a protocol to run an inter-laboratory ring test to validate the methodology at the end of 2015.

The second phase of the development of methods is to measure disinfection efficacy of the cyst form of *Acanthamoeba*. Procedures and protocols have not been finalized inside the expert community. In general numerous workers have published results for disinfection efficacy against *Acanthamoeba* species. Given the non-standard testing conditions; some differences have been reported.

Currently, even with two microbiology workshops and recommendations from ophthalmic panel meetings, there are no testing requirements for *Acanthamoeba* required during the approval of a disinfection in the United States. At this time even the procedure for the evaluation of products causing encystment (ISO 18259) has not been adopted in the US. However, there is a perceived need to have care systems that are "effective" against *Acanthamoeba*.

While encystment was related to the recall of a product in 2007, there are no criteria in the ISO standard 18259. Any new product should not cause any significant encystment under test protocol.

Beyond the difficulty in finding appropriate testing methodology, setting appropriate criteria for effectiveness have not been addressed. There are three different types of organisms that are a concern in lens care—bacteria, fungi and amoeba. They occur in significantly different rates. The overall observed rate for all organisms in daily wear is approximately 4 in 10,000, and 20 per 10,000 in extended wear. Most frequently bacterial infections are observed followed by fungi at much lower levels. As a comparison the incidence of Acanthamoeba infections are nearly 200 to 1000 times less frequent than the overall infection rate. In terms of the ability of most disinfection, bacteria are more easily eliminated compared to fungi and both much more easily eliminated compared to Acanthamoeba; especially the cyst form.

The current primary acceptance criteria in the global standard, ISO 14729, for bacteria is a reduction of an inoculum of approximately one million ($10^6$)/ml by three log to one thousand/ml ($10^3$). Fungi are expected to be reduced one log from approximately 1 million ($10^6$) to one hundred thousand ($10^5$); or one log. If products do not meet the primary criteria, they can be acceptable for use in a disinfection regimen by qualifying by demonstrating disinfecting activity for bacteria and stasis for fungi followed by a simulated use of the product. In the development of criteria, given the requirements for efficacy against fungal organisms and the higher risk, justifying requirements for Acanthamoeba equal to or of above the requirements for fungi in current standards may be difficult.

The current approaches in the draft of ISO19045-218 to testing the disinfection efficacy are undergoing interlaboratory evaluations for trophozoites. The inoculum for these tests is lower ($10^4$-$10^5$) than that used for bacteria and fungi. While no criteria has been identified, a reduction of at least one log would be desirable for reduction of trophozoites under test with the solution, and no growth or stasis for inclusion in a simulated use test where the recovery is less the 10 organisms/ml in the general procedure outlined in 14729. Results from testing under the conditions suggested in ISO 18259 should show reduction and no increase with lenses and cases over time.

At this time there are no accepted protocols for disinfection of Acanthamoeba cysts. It is expected that the major considerations in developing methodology will be the process for forming the cyst form. It is likely that the inoculum levels will be determined by results obtained in the evaluations used for the ISO 19045-1 and 19045-2. Since the cyst is much more resistant to disinfection the disinfection efficacy is likely to be lower than that obtained with trophozoites. This presents a difficulty. Cyst forms of Acanthamoeba can revert to the trophozoite form and both are potentially infective. Ideally products would have similar disinfection efficacy for both trophozoite and cyst forms.

In the United States, there continues to be no requirement for testing Acanthamoeba even though recommended at the microbiology workshops and by the Ophthalmic Panel. Researchers have evaluated products, and many manufacturers have studied their own products and competitive products for activity under a number of different testing protocols.

In Europe, manufacturers having suitable data, have included claims for effectiveness for efficacy against Acanthamoeba on the product label. Other jurisdictions vary in their acceptance of specific claims.

Hydrogen peroxide ($H_2O_2$) is a widely accepted disinfectant that is used in a number of settings including disinfection of contact lenses. Although some activity has been demonstrated against acanthamoeba, only limited log reductions after long contact times have been reported with 3% $H_2O_2$ systems which employ concurrent peroxide neutralization schemes. Due to the risk of acanthamoeba keratitis, a system that can demonstrate much greater activity in this area would be advantageous having the potential to create a claim supported competitive advantage.

SUMMARY

In one aspect, the present disclosure relates to a method for disinfecting contact lenses, including immersing the contact lenses in a volume of cleaning agent with about 3% hydrogen peroxide for up to 4 hrs, and immersing up to 0.7 g of a fibrous catalyst enhancer material in the volume of cleaning agent for up to 4 hrs. The fibrous catalyst enhancer material is immersed simultaneously with the contact lenses.

DESCRIPTION OF EXAMPLE EMBODIMENTS

An example embodiment relates to a method of killing and/or inactivating microbes (such as spores, bacteria, viruses, parasites, fungi and yeast) using a catalyst comprising a solid support, which solid support comprises one or more fibers, and a metal cation fixed to the support, to a method of disinfecting a substrate, for example a contact lens, using the catalyst, to the use of the catalyst for killing and/or inactivating microbes and for disinfecting a substrate, and to a composition and an apparatus for killing and/or inactivating microbes comprising the catalyst.

For the avoidance of doubt, by the term "fibrous catalyst" we mean a catalyst that comprises polymer fibers to which catalytically active sites or centers are attached. By the term "fibers" we include both a single monofilament and a complex filament that is made up of more than one monofilament. An example fibrous catalyst can be any fabric that includes polyacrylonitrile (hereinafter "PAN") fibers. The references herein to a fabric may refer simply to an arrangement of one or more PAN fibers. In one aspect of the invention, the fabric that comprises PAN fibers is a knitted fabric, such as a fibrous knitted mesh. Thus, in this aspect, the PAN fibers/yarn are capable of being knitted. The knitted fabric may be prepared by any suitable method known in the art.

The example fibrous catalyst can be prepared using a process including the steps of: (i) treating a fabric comprising polyacrylonitrile fibers with a hydrazine salt selected from hydrazine sulfate and dihydrazine sulfate (especially dihydrazine sulfate) and hydroxylamine sulfate in the presence of a base to provide a modified fabric; (ii) treating the modified fabric with a base; and (iii) treating the modified fabric with an aqueous solution comprising a sulfate salt of an iron cation and a salt (especially a sulfate, nitrate and/or chloride salt, more especially a sulfate and/or chloride salt, most especially a sulfate salt) of a second metal cation, wherein the second metal cation is selected from a lithium, sodium, potassium, magnesium, calcium and zinc cation, and mixtures thereof. Example fibrous catalysts used in the described method can include fibrous catalysts described in U.S. Pat. Nos. 8,410,011, 8,513,303 and U.S. Patent Application Number 2011/0098174, each of which is hereby incorporated by reference.

In an example embodiment, the method includes simultaneously immersing contact lenses in a volume of cleaning agent solution composed of about 10 ml of about 3% hydrogen peroxide and also immersing up to 0.7 g of a fibrous catalyst enhancer material in the volume of cleaning agent solution for up to 4 hours. More preferably, the contact lenses and fibrous catalyst enhancer material are immersed in the cleaning agent solution for between 2 and 4 hours. The ratio of this volume of cleaning solution (approximately 10 ml) to 0.7 g fibrous catalyst produces a maximum catalytic effect. The fibrous catalyst enables a stable equilibrium in hydrogen peroxide, thus creating stable hydroxyl groups, which are superior to hydrogen peroxide in their ability to kill microbes.

Preferably, between 0.4 and 0.7 g of the fibrous catalyst enhancer is immersed in the cleaning agent solution. More preferably, about 0.5 g of the fibrous catalyst enhancer is immersed in the cleaning agent solution.

Preferably, the fibrous catalyst enhancer material is composed of fabric. More preferably, the fibrous catalyst enhancer material includes an iron cation. More preferably still, the fibrous catalyst enhancer material includes up to 22,000 µg of iron cation per gram of fabric. In particular, the fibrous catalyst enhancer material includes up to 10000 µg of iron cation per gram of fabric, and more preferably up to 9000 µg of iron cation per gram of fabric. Below this concentration, the generation of hydroxyl radicals is insufficient to bring about superior microbial efficacy. Below this ratio, the number of active catalytic centers are insufficient to generate the hydroxyl radicals necessary to create the superior microbicidal efficacy in a dynamic disinfection system; one in which the hydrogen peroxide concentration is being eliminated by a separate Pt element or catalyse enzyme. As this type of "single step" hydrogen peroxide system is most preferred, this ratio allows one to create the necessary micro-environment to create superior microbicidal efficacy.

The volume of cleaning agent solution is defined within an enclosure with a removable seal. The fibrous catalyst enhancer material is removably supported by a basket that is immersed in the volume of cleaning agent solution. The basket is supported by the seal. The volume of cleaning agent solution is preferably between 5 mL and 15 mL, more preferably between 5 mL and 11 mL and most preferably between 9 mL and 11 mL. This concentration of hydrogen peroxide provides adequate microbial efficacy for traditional peroxide solutions which undergo simultaneous neutralization to oxygen and water. For ease of submerging two separate contact lenses, and their respective left-eye and right-eye designated holders, it is found that this volume/size is effective.

The method additionally includes neutralizing the cleaning agent solution, for example by immersing a platinum neutralizing element in the volume of cleaning agent solution and/or exposing the contact lenses and fibrous catalyst enhancer to a volume of isotonic, buffer saline. An example isotonic, buffer saline can include a neutralizing enzyme such as catalase. Preferably, the cleaning agent solution is neutralized while the contact lenses and fibrous catalyst enhancer material are immersed in the volume of cleaning agent solution.

Figure 1:
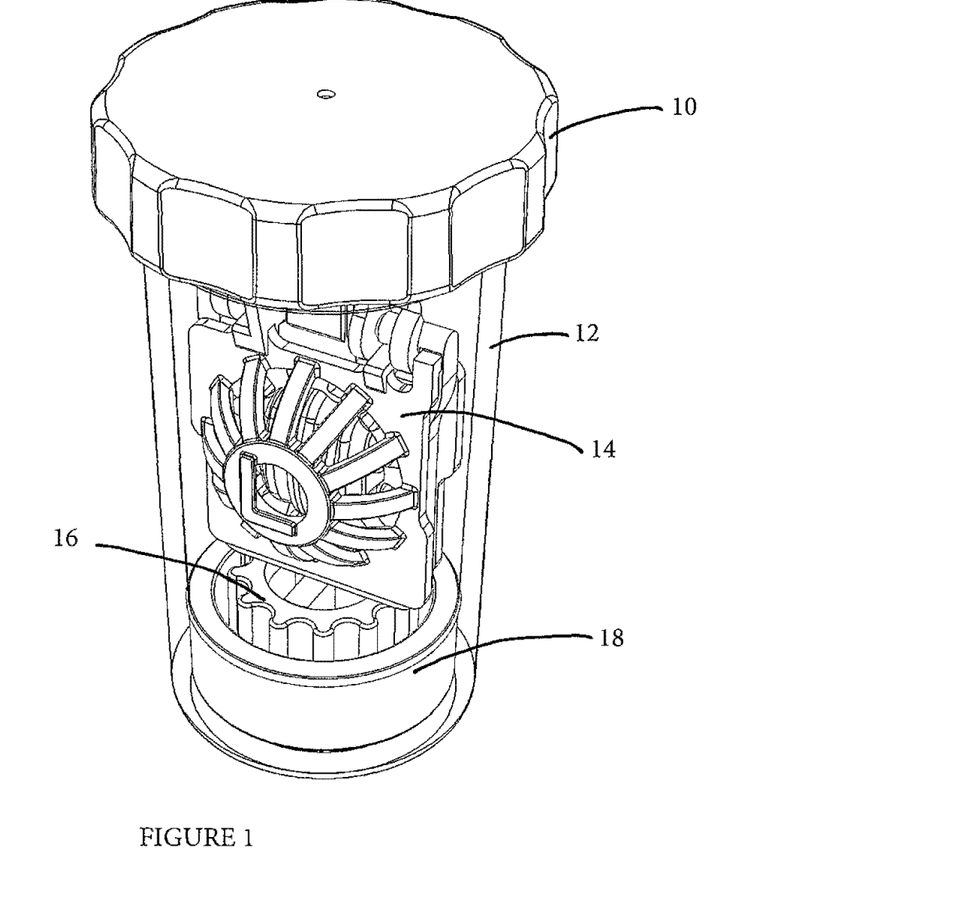
FIG. 1 illustrates a top and side perspective view of a system for cleaning ophthalmic lenses, including a cup, a lens support and a fibrous catalyst.
Figure 2:
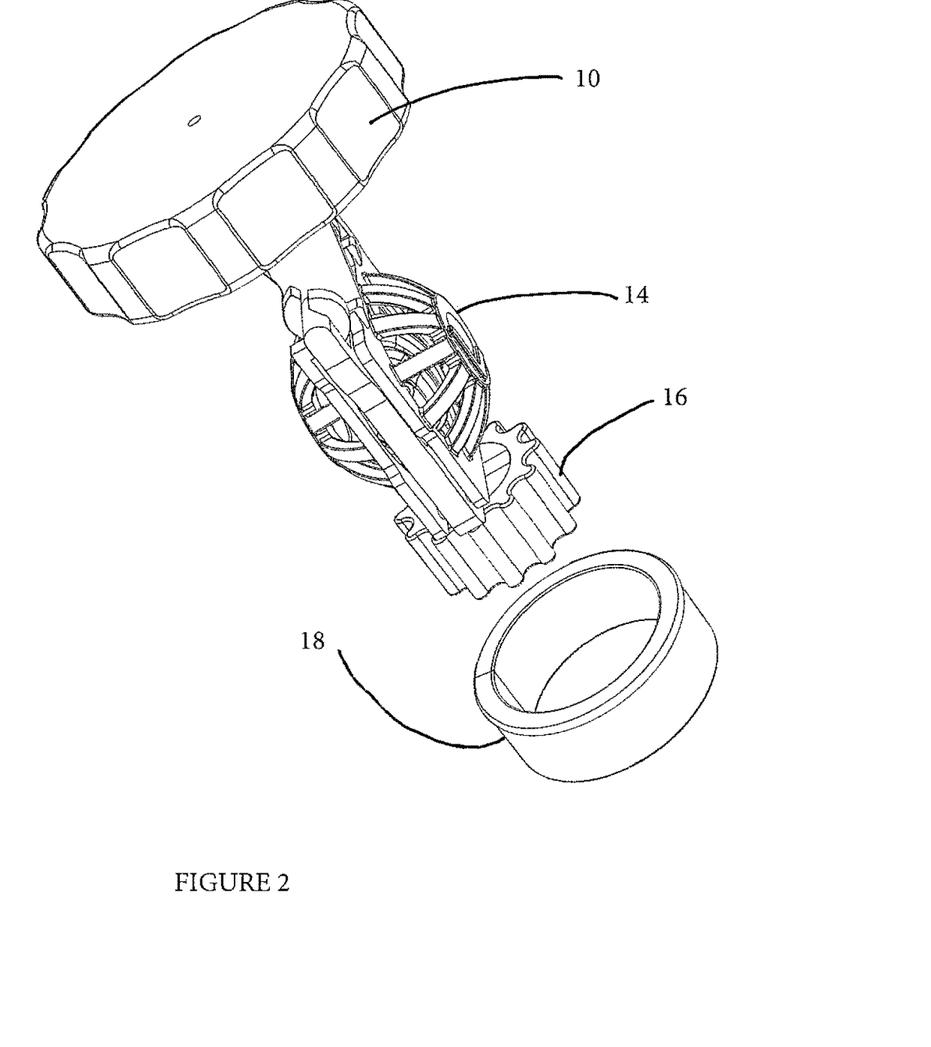
FIG. 2 illustrates a side perspective view of the lens support and fibrous catalyst shown in FIG. 1 without the cup, showing the fibrous catalyst removed from the lens support.

FIGS. 1-2 illustrate an example system for performing the above-described cleaning process. The illustrated system includes a lid 10 that connects with a cup 12, preferably to form a seal. The lid 10 can sealingly connect with the cup 12 through any mechanism that forms a seal, for example a snap-fit and corresponding threading similarly to the containers described in U.S. Pat. Nos. 6,945,389 and 8,767,367 both hereinafter incorporated by reference. A basket 14 extends from and is supported by the lid 10. In use the cage 14 receives ophthalmic lenses and is inserted within the cup 12. A neutralizing ring 16 is supported at the distal free end of the cage 14. The neutralizing ring 16 can comprise platinum.

A fibrous catalyst 18 element is depicted to be supported by the cage 14 structure, for example around the neutralizing ring 16. The depicted fibrous catalyst 18 can have a ring shape allowing for a removably snug fit around the neutralizing ring 16. The fibrous catalyst 18 can be comprised of the fibrous catalyst material described above for use with cleaning ophthalmic lenses.

In use, the cup 12 is filled with a cleaning solution, for example hydrogen peroxide as described above. The cage 14 is inserted into the hydrogen peroxide in the cup 12 such that the ophthalmic lenses are immersed. The fibrous catalyst 18 reacts with the hydrogen peroxide to clean the ophthalmic lenses, as described above. The neutralizing ring 16 neutralizes the hydrogen peroxide, as described above.

Figure 3:
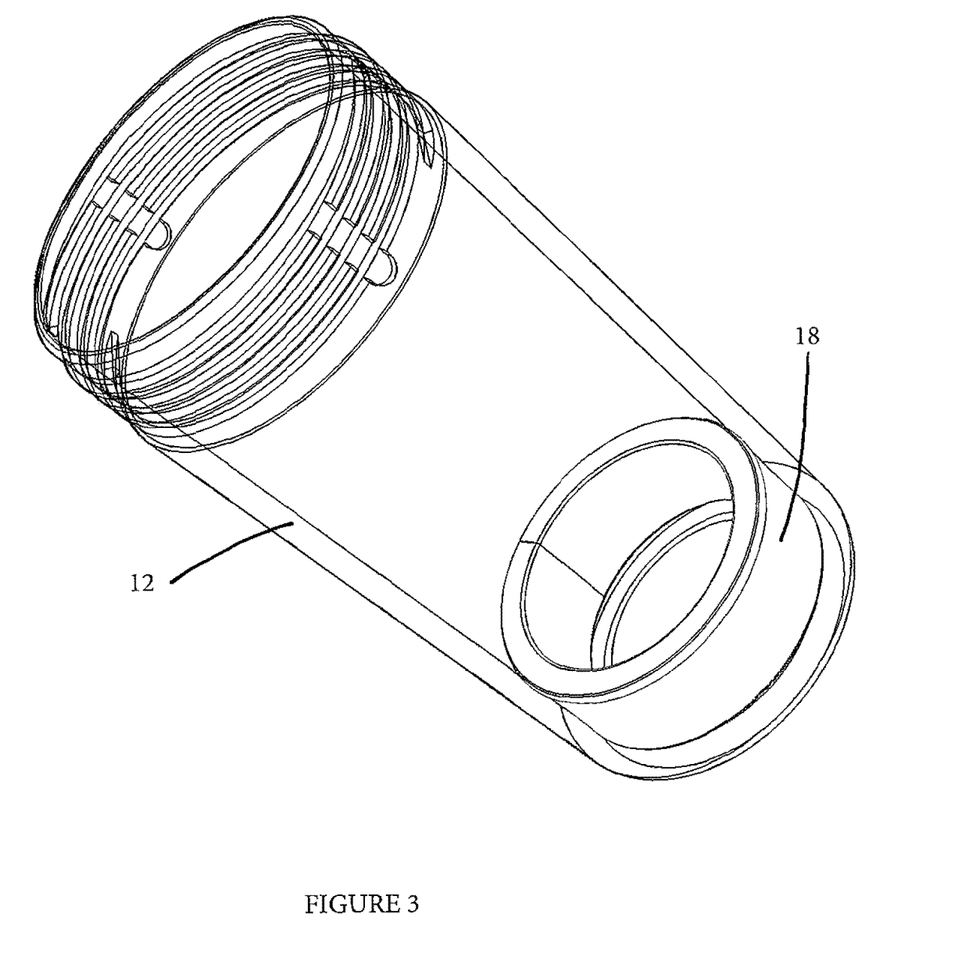
FIG. 3 illustrates a side perspective view of the cup and the fibrous catalyst shown in FIG. 1 without the seal and basket, show in an alternative embodiment with the fibrous catalyst being removably supported by the cup.

Alternatively, as illustrated in FIG. 3, the fibrous catalyst 18 can be removably supported within the cup 12. The fibrous catalyst 18 can be supported within the cup 12 with a friction fit, adhesive, or any other method understood by one of ordinary skill in the art to allow the fibrous catalyst to remain in the cup. In use, the cage 14 is inserted into the cup 12, and the neutralizing ring 16 is inserted within the annular shape of the fibrous catalyst 18.

COMPARATIVE EXAMPLES

FIGS. 4-8 illustrate studies performed to evaluate the efficacy of commercial one-step hydrogen peroxide contact lens care solutions against the trophozoites and cysts of *Acanthamoeba*, and to determine whether the addition of a catalyst enhancing material increased the efficacy of disinfection.

In the described examples, the *A. castellanii* (ATCC 50370) and *A. polyphaga* (ATCC 30461) strains were isolated from *Acanthamoeba keratitis* cases but differed in their genetic and morphological characteristics. The forms of the strains were trophozoites and cysts. The trophozoites were grown in Ac#6 medium and the cysts were formed on non-nutrient agar.

Bausch+Lomb PeroxiClear® solution (3% hydrogen peroxide with a platinum disc neutralizing system) and AOSept® Plus solution (3% hydrogen peroxide with a platinum disc neutralizing system) were the test systems. ¼ Strength Ringer's solution was used as a negative control. The disinfectant neutraliser was 500 U/ml catalase in ¼ Strength Ringer's solution.

Testing was performed using a most probable number approach to quantify trophozoite or cyst viability after exposure to the disinfectant solutions for 2, 4, 6 and 24 hours at 25° C. Ten ml of the above-described commercial hydrogen peroxide systems with or without 0.5 g of the catalyst enhancer material ("fabric"). When testing with cysts, aliquots were removed at 1, 2, 4 and 6 hour intervals and the number of surviving organisms determined. With trophozoites, rapid killing occurs in the hydrogen peroxide systems and the sample time points were reduced to 5, 10, 15 and 30 minutes.

Figure 4:
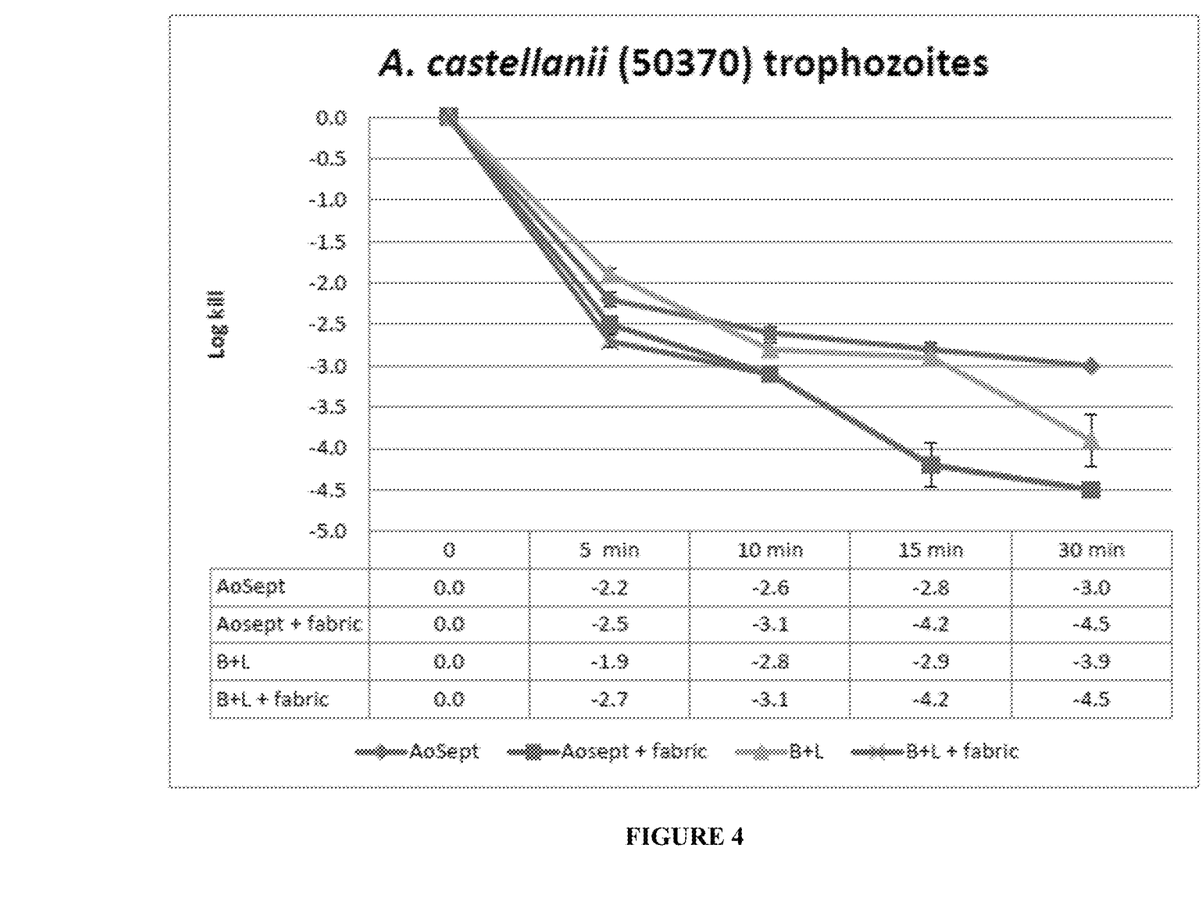
FIG. 4 illustrates the efficacy of test systems against A. castellanii (ATCC 50370) trophozoites.

FIG. 4 shows illustrates that for the trophozoites of *A. castellanii* (50370), the AOSept® system gave a 3.0 log 10 kill after 30 minutes exposure compared to 4.5 log 10 kill in the presence of the fabric (P<0.001). Similarly, the Bausch+Lomb system showed a 3.9 log 10 kill after 30 minutes compared to 4.5 log 10 kill when the fabric was included (P<0.001).

Figure 5:
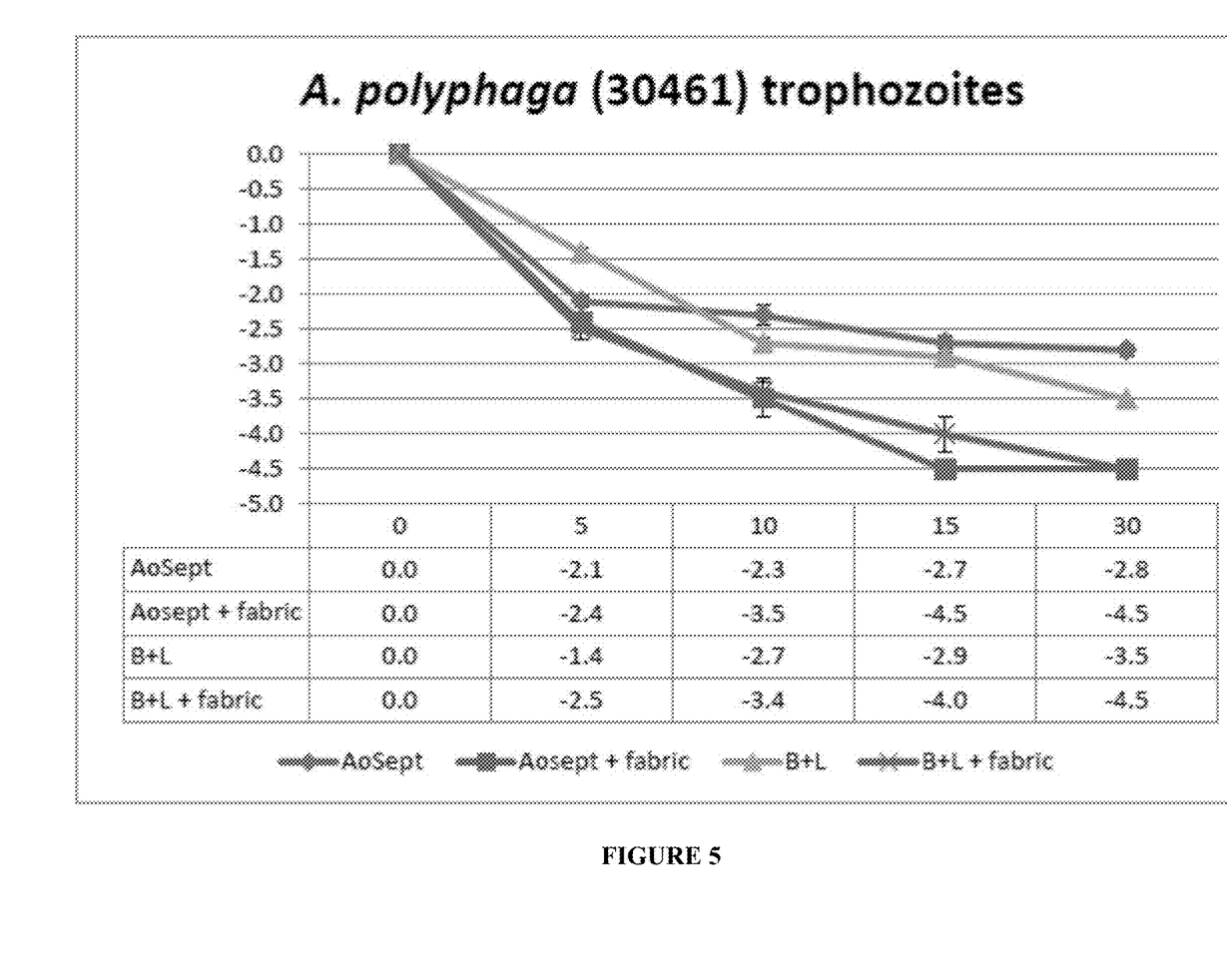
FIG. 5 illustrates the efficacy of test systems against A. polyphaga (ATCC 30461) trophozoites.

FIG. 5 illustrates that for the trophozoites of *A. polyphaga* (30461), the AOSept® system gave a 2.8 log 10 kill after 30 minutes exposure compared to 4.5 log 10 kill in the presence of the fabric (P<0.001). Similarly, the Bausch+Lomb system showed a 3.5 log 10 kill after 30 minutes compared to 4.5 log 10 kill when the fabric was included (P<0.001).

Figure 6:
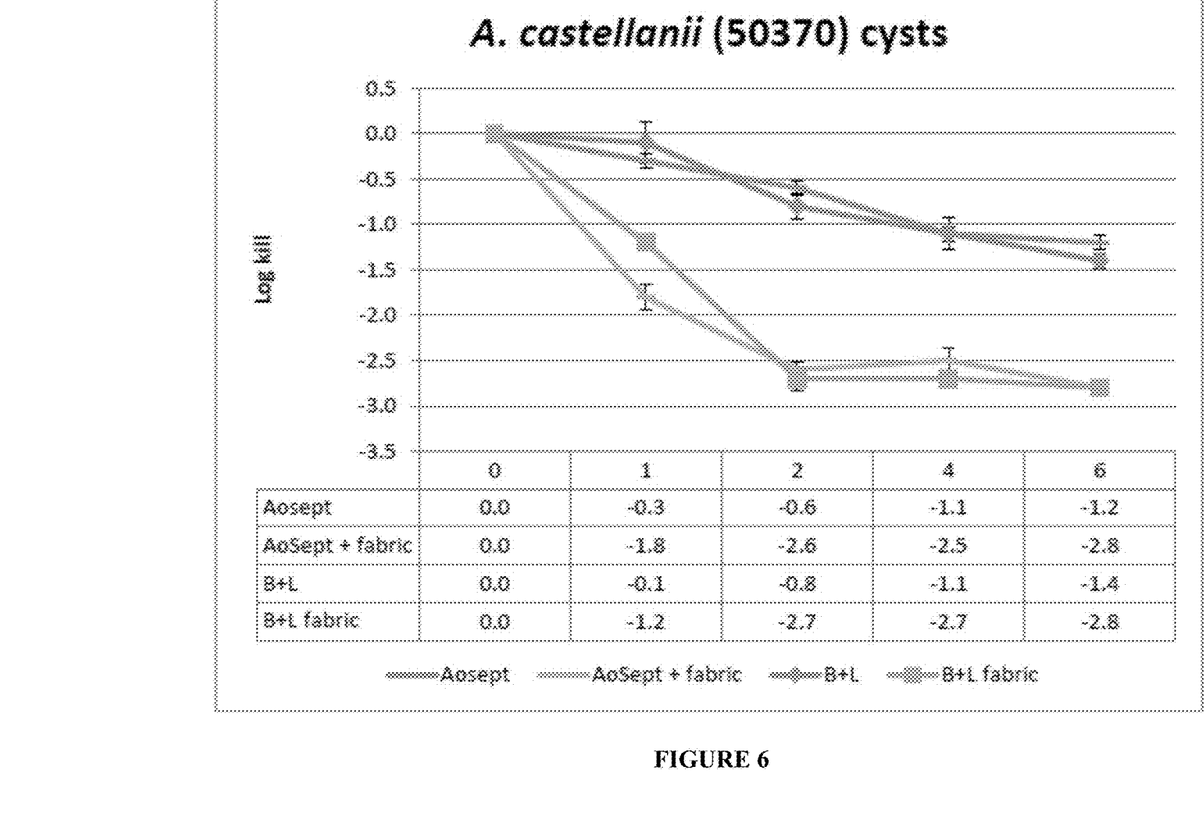
FIG. 6 illustrates the efficacy of test systems against A. castellanii (ATCC 50370) cysts.

FIG. 6 illustrates that for the cysts of *A. castellanii* (50370), the AOSept® system gave a 1.2 log 10 kill after 6 hours exposure compared to 2.8 log 10 kill in the presence of the fabric (P<0.001). Similarly, the Bausch+Lomb system showed a 1.4 log 10 kill after 6 hours compared to 2.8 log 10 kill when the fabric was included (P<0.001).

Figure 7:
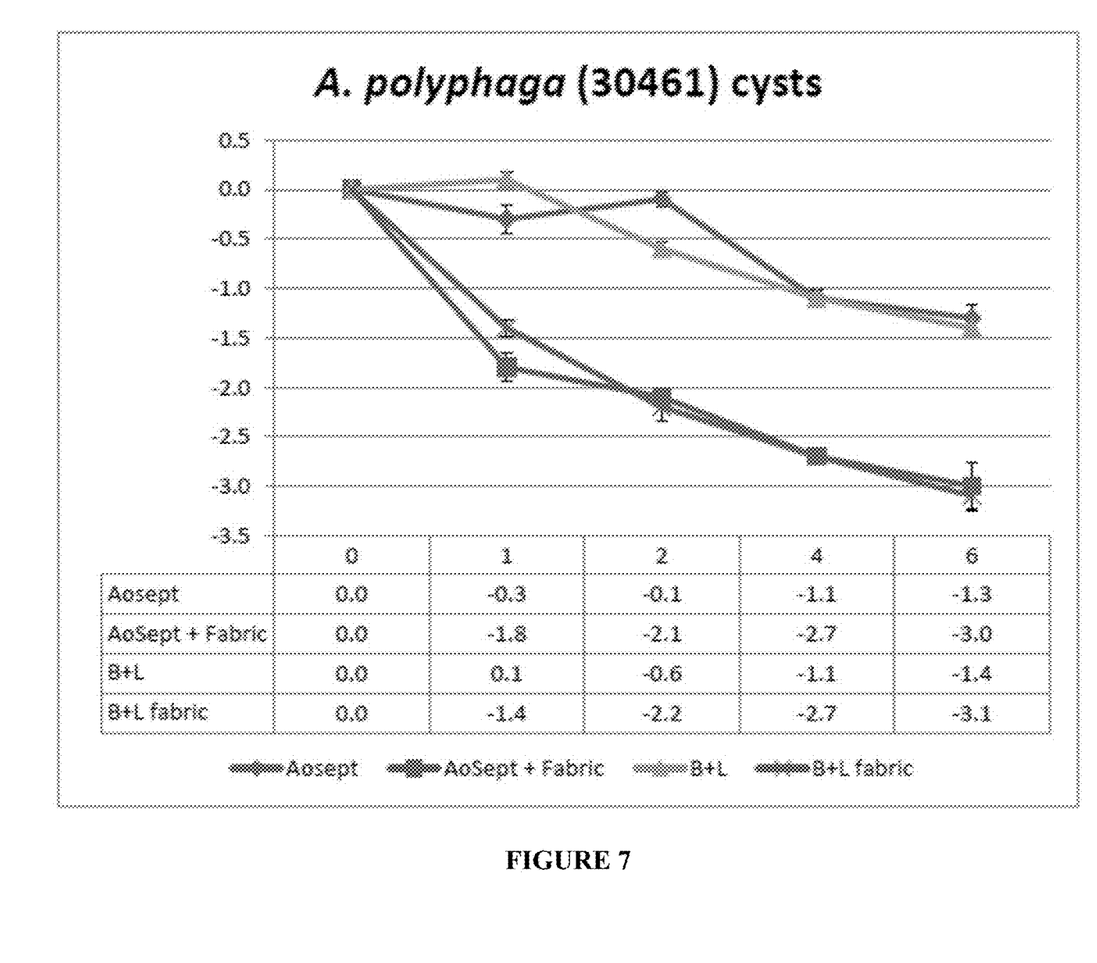
FIG. 7 illustrates the efficacy of test systems against A. polyphaga (ATCC 30461) cysts.

FIG. 7 illustrates that for the cysts of *A. polyphaga* (30461), the AOSept® system gave a 1.3 log 10 kill after 6 hours exposure compared to 3.0 log 10 kill in the presence of the fabric (P<0.001). Similarly, the Bausch+Lomb system showed a 1.4 log 10 kill after 6 hours compared to 3.1 log 10 kill when the fabric was included (P<0.001).

Incubation of trophozoites or cysts of the *Acanthamoeba* strains in ¼ strength Ringer's solution and 0.5 g of the fabric for 6 hours showed significant reduction in viability ($\leq 5$ log 10 reduction, results not shown). The catalyst enhancing fabric significantly increased the efficacy of both commercial hydrogen peroxide one-step contact lens disinfectant systems.

Figure 8:
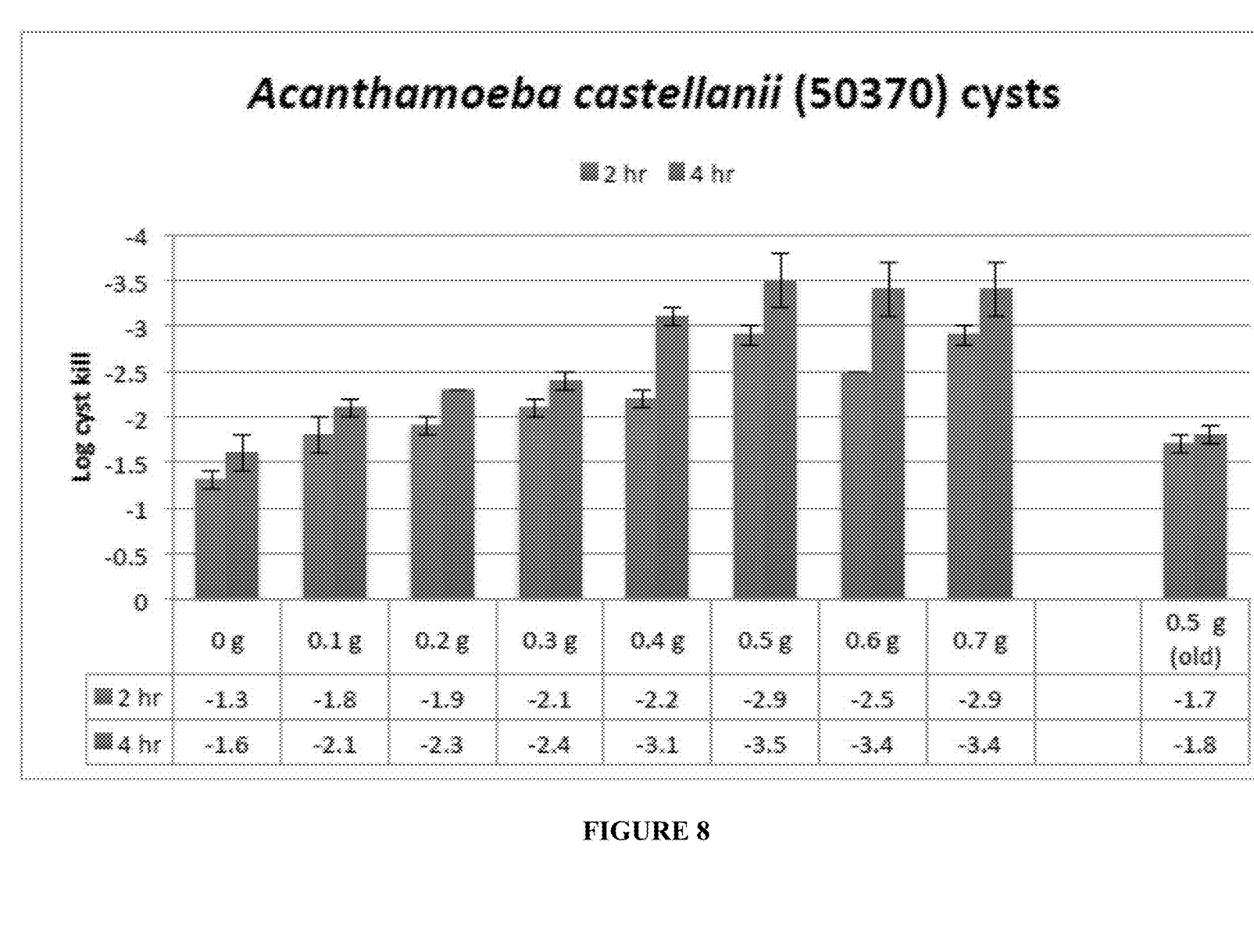
FIG. 8 illustrates the efficacy of test systems against A. castellanii (ATCC 50370) cysts and compares the efficacy of exposure to the catalyst after 2 hours and 4 hours.

FIG. 8 illustrates an additional study performed to evaluate the efficacy of a commercial one-step hydrogen peroxide contact lens care system against the cysts of *Acanthamoeba castellanii* and to determine the influence of varying amounts of catalyst enhancing material on the degree of kill.

In the described example, the *A. castellanii* (ATCC 50370) strain was isolated from an *Acanthamoeba keratitis* clinical case (clinical strain). The forms of the strains were trophozoites and cysts. The trophozoites were grown in Ac#6 medium and the cysts were formed on non-nutrient agar, as described previously.

AOSept® Plus (3% hydrogen peroxide with a platinum disc neutralizing system) were the test system. ¼ Strength Ringer's solution was used as a negative control. The disinfectant neutraliser was 500 U/ml catalase in ¼ Strength Ringer's solution.

Testing was performed as described previously, using a most probable number approach to quantify cyst viability after exposure to the disinfectant solutions for 2 and 4 hours at 25° C. 10 ml of AOSept® Plus with platinum neutralizing disc and 0.0-0.7 g of the catalyst enhancer material ("fabric") was investigated. In addition, the older version of the fabric (0.5 g) was also compared.

FIG. 7 illustrates the efficacy of the test solutions, with and without the various weights of fabric against the cysts of *A. castellanii* (50370) after 2 and 4 hours exposure is shown in FIG. 1. The AOSept® system alone gave a 1.3-1.6 log 10 kill after 2-4 hours exposure. In the presence of the fabric, a steady increase in cyst kill was observed with 0.1-0.4 g of material, giving a 1.8-2.2 log 10 kill at 2 hours and 2.1-3.1 log 10 kill after by 4 hours. Maximum increased kill occurred with 0.5 g of material with 2.9 and 3.5 log 10 kill at 2 and 4 hours, respectively. No additional kill was observed when 0.6 g and 0.7 g of material was tested. When 0.5 g of the older type of material tested, less killing was observed with 1.7-1.8 log 10 kill at 2 and 4 hours, respectively. Addition of the catalyst enhancing fabric gradually increased the efficacy of the AOSept® system at a concentration of 0.1-0.4 g, achieving significantly enhanced cyst kill at 0.5 g.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

I claim:

1. A method for disinfecting contact lenses, the method comprising:
    immersing the contact lenses in a volume of cleaning agent comprising about 3% hydrogen peroxide for up to 4 hrs; and
    increasing the disinfection efficacy of and creating stable hydroxyl groups in the hydrogen peroxide by immersing up to 0.7 g of a fibrous catalyst enhancer material in the volume of cleaning agent for up to 4 hrs, the fibrous catalyst enhancer material being immersed simultaneously with the contact lenses, wherein the fibrous catalyst enhancer material comprises covalently attached iron cation.

2. The method of claim 1, wherein the contact lenses and fibrous catalyst enhancer material are each immersed in the cleaning agent for between 2 and 4 hrs.

3. The method of claim 1, wherein the immersing step comprises immersing between 0.4 and 0.7 g of the fibrous catalyst enhancer in the cleaning agent.

4. The method of claim 3, wherein the immersing step comprises immersing about 0.5 g of the fibrous catalyst enhancer in the cleaning agent.

5. The method of claim 1, wherein the fibrous catalyst enhancer material comprises a fabric.

6. The method of claim 5, wherein the fibrous catalyst enhancer material comprises up to 22,000 μg of iron cation per gram of fabric.

7. The method of claim 6, wherein the fibrous catalyst enhancer material comprises up to 10000 μg of iron cation per gram of fabric.

8. The method of claim 6, wherein the fibrous catalyst enhancer material comprises at least 9000 μg of iron cation per gram of fabric.

9. The method of claim 8, wherein the volume of cleaning agent comprises between 5 and 10 mL.

10. The method of claim 8, wherein the volume of cleaning agent comprises between 9 and 11 mL.

11. The method of claim 1, wherein the volume of cleaning agent comprises between 5 and 15 mL.

12. The method of claim 1, wherein the volume of cleaning agent is defined within an enclosure comprising a removable seal.

13. The method of claim 12, wherein the fibrous catalyst enhancer material is removably supported by a basket that is immersed in the volume of cleaning agent, wherein the basket is supported by the seal.

14. The method of claim 1, further comprising neutralizing the cleaning agent with a neutralizing element that is separate from the fibrous catalyst enhancer material.

15. The method of claim 14, wherein neutralizing the cleaning agent comprises immersing a platinum neutralizing element in the volume of cleaning agent.

16. The method of claim 14, wherein neutralizing the cleaning agent comprises exposing the contact lenses and fibrous catalyst enhancer to a volume of isotonic, buffer saline.

17. The method of claim 16, wherein isotonic, buffer saline comprises a neutralizing enzyme.

18. The method of claim 17, wherein the neutralizing enzyme is catalase.

19. The method of claim 14, wherein the neutralizing step occurs while the contact lenses and fibrous catalyst enhancer material are immersed in the volume of cleaning agent.

20. The method of claim 1, wherein the fibrous catalyst enhancer comprises an annular shape.

21. The method of claim 1, wherein the fibrous catalyst enhancer is removably supported within the volume of cleaning agent.

22. The method of claim 1, wherein the fibrous catalyst is prepared by a process comprising:
treating a fabric comprising polyacrylonitrile fibers with a hydrazine salt to provide a modified fabric; and
treating the modified fabric with an aqueous solution comprising a sulfate salt of an iron cation.

23. The method of claim 1, further comprising enabling a stable equilibrium in the hydrogen peroxide by immersing the fibrous catalyst enhancer material in the volume of cleaning agent.

24. A method for disinfecting contact lenses, the method comprising:
immersing the contact lenses in a volume of cleaning agent comprising about 3% hydrogen peroxide for up to 4 hrs; and
increasing the disinfection efficacy of and enabling a stable equilibrium in the hydrogen peroxide by immersing up to 0.7 g of a fibrous catalyst enhancer material in the volume of cleaning agent for up to 4 hrs, the fibrous catalyst enhancer material being immersed simultaneously with the contact lenses, wherein the fibrous catalyst enhancer material comprises covalently attached iron cation.

25. The method of claim 24, wherein:
the volume of cleaning agent is defined within an enclosure comprising a removable seal;
the fibrous catalyst enhancer material is removably supported by a basket that is immersed in the volume of cleaning agent; and
the basket is supported by the seal.

26. The method of claim 24, further comprising neutralizing the cleaning agent with a neutralizing element that is separate from the fibrous catalyst enhancer material,
wherein neutralizing the cleaning agent comprises immersing a platinum neutralizing element in the volume of cleaning agent.

27. The method of claim 24, wherein the fibrous catalyst enhancer is removably supported within the volume of cleaning agent.

* * * * *